United States Patent [19]
Samain et al.

[11] Patent Number: 6,024,948
[45] Date of Patent: *Feb. 15, 2000

[54] HAIR SHAPING COMPOSITION COMPRISING A FILM-FORMING ACRYLIC OLIGOMER

[75] Inventors: Henri Samain, Bièvres; Nathalie Mougin, Paris, both of France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/710,858

[22] Filed: Sep. 23, 1996

[30] Foreign Application Priority Data

Sep. 21, 1995 [FR] France ................... 95 11110

[51] Int. Cl.$^7$ ........................................... A61K 7/11
[52] U.S. Cl. ..................... 424/70.16; 424/70.11; 424/70.1
[58] Field of Search ............... 424/70.16, 70.11, 424/70.1

[56] References Cited

U.S. PATENT DOCUMENTS

| | | | |
|---|---|---|---|
| 4,085,264 | 4/1978 | Seib et al. | 526/97 |
| 5,019,377 | 5/1991 | Torgerson | 424/70.16 |
| 5,104,642 | 4/1992 | Wells et al. | 424/47 |
| 5,306,484 | 4/1994 | Potthoff-karl et al. | 424/47 |
| 5,362,415 | 11/1994 | Egraz | 252/174.24 |
| 5,413,775 | 5/1995 | Hatfield et al. | 424/47 |
| 5,501,851 | 3/1996 | Mudget et al. | 424/70.16 |
| 5,589,157 | 12/1996 | Hatfield | 424/47 |
| 5,599,532 | 2/1997 | Faryniarz et al. | 424/70.16 |

FOREIGN PATENT DOCUMENTS

| | | |
|---|---|---|
| 0 379 082 | 1/1990 | European Pat. Off. . |
| 0 590 604 | 9/1993 | European Pat. Off. . |
| 2 351 135 | 5/1977 | France . |
| 43 14 305 | 4/1993 | Germany . |

OTHER PUBLICATIONS

*Chemical Abstracts*, vol. 89, No. 14 (1978), p. 517, abstract No. 117546m, "Hair Setting Preparations."

*Primary Examiner*—Thurman K. Page
*Assistant Examiner*—Brian K. Seidleck
*Attorney, Agent, or Firm*—Finnegan, Henderson, Farabow, Garrett & Dunner, L.L.P.

[57] ABSTRACT

Compositions for hair shaping and/or form retention of hair comprising, in a cosmetically acceptable aqueous medium, at least one film-forming acrylic oligomer, which is soluble or dispersible in the aqueous medium, having a molecular weight, measured by steric exclusion chromatography, of less than or equal to 50,000 and with a glass transition temperature Tg ranging from 0 to 45° C. preferably comprising:

a) from 20 to 45% by weight of at least one residue of a monomer (A) selected from tert-butyl methacrylate, tert-butyl acrylate, and isobutyl methacrylate, relative to the total weight of the at least one film-forming acrylic oligomer;

b) from 5 to 25% by weight of at least one residue of monomer (B) with ethylenic unsaturation comprising at least one carboxylic acid functional group, relative to the total weight of the at least one film-forming acrylic oligomer; and c) at least one residue of monomer (C) comprising a $(C_1-C_4)$alkyl acrylate, in an amount sufficient to produce an oligomer having a Tg temperature ranging from 0 to 45° C., wherein the at least one monomer (C) is not tert-butyl acrylate.

35 Claims, No Drawings

HAIR SHAPING COMPOSITION COMPRISING A FILM-FORMING ACRYLIC OLIGOMER

A subject of the present invention is aqueous compositions for hair shaping and/or form retention of hair comprising, in a cosmetically acceptable aqueous medium, at least one film-forming acrylic oligomer which is soluble or dispersible in the medium, and its uses.

Film-forming polymers which are soluble in aqueous and aqueous/alcoholic media, such as polyvinylpyrrolidone, vinylpyrrolidone/vinyl acetate copolymers, vinyl acetate/crotonic acid copolymers or anionic or amphoteric acrylic resins, are commonly used in products for hair shaping and/or form retention of the hairstyle.

The most widespread hair products on the cosmetics market for hair shaping and/or form retention of the hairstyle are sprayable compositions composed of a solution, most often an aqueous/alcoholic solution, and of a film-forming polymer which is soluble in the water and in the alcohol, such as those mentioned above, as a mixture with various cosmetic adjuvants. This solution is generally packaged either in an appropriate aerosol container pressurized using a propellant gas or in a pump-action spray.

For a number of years, very particular interest has been shown in aerosol lacquers or pump-action sprays with high water concentrations "with a high solids content" of film-forming polymer.

Throughout the description, aerosol or pump-action spray with "a high solids content" of lacquering product will be understood to mean any aqueous formulation packaged in one of these forms containing more than 5 weight %, on a dry basis, of lacquering product with respect to the total weight of the formulation.

On the one hand, attempts are being made to decrease the concentrations of compounds which are volatile at atmospheric pressure, known as VOCs (Volatile Organic Compounds), present in sprayable compositions in the aerosol or pump-action spray form.

In fact, the use of alcohol, alone or as a mixture with a small amount of water, as well as the use of propellant gases, can exhibit a number of disadvantages, such as an increase in flammability or environmental pollution.

VOCs are mainly propellant gases, such as hydrocarbons or dimethyl ether (DME), and solvents, such as ethanol.

On the other hand, attempts are being made to reduce the drying times of the sprayed product and to increase its lacquering power after spraying onto hair. The use of water-soluble film-forming polymers in aerosols or pump-action sprays with high water concentrations, in particular in water/ethanol/dimethyl ether spraying systems having a maximum VOC level of 55%, requires higher concentrations, on a dry basis, of polymer with respect to those used in organic spraying systems (100% VOC) in order to obtain satisfactory fixing powers and drying times.

In fact, an increase in the concentration of water in aerosol or pump-action spray packagings results in a large decrease in the lacquering power and in much longer drying times.

The film-forming polymers commonly used in compositions of this type have molecular weights, measured by steric exclusion chromatography, which are generally greater than 50,000 and preferably greater than 100,000. Increasing their concentration in aerosol or pump-action spray lacquers with high water contents results in excessively high viscosities, so that it is no longer possible to obtain satisfactory spraying of the product at the outlet of the aerosol or of the pump-action spray.

One solution, in order to overcome these problems of viscosity of the "juice" in the spraying device, would consist in using film-forming oligomers which are soluble or dispersible in the medium of the sprayable composition, introducing low viscosity.

Presently, the majority of oligomers, with a molecular weight of less than 50,000, that are used in products for form retention of hair exhibit mechanical properties which are insufficient for obtaining a satisfactory lacquering power, even at high concentrations.

When oligomers, with a molecular weight of less than 50,000, are used in the latex form (dispersion of particles), they have a tendency to produce, at the sprayer outlet, a spray or a lacquer with an off-white appearance which is not very desirable for cosmetic purposes and also to be difficult to remove on shampooing.

The inventors have surprisingly discovered that, by using certain film-forming acrylic oligomers with a molecular weight of less than or equal to 50,000 and with a glass transition temperature Tg ranging from 0 to 45° C., which are soluble or dispersible in aqueous media, it was possible to produce aerosol lacquers or pump-action sprays with a high solids content of lacquering agent having a good diffusion during application, a good lacquering power, a good rate of drying and good cosmetic properties, in particular as regards feel and disentangling.

These specific oligomers, which will be defined later, are very particularly suitable for aerosol hair compositions with "a high solids content" of the water/ethanol/DME type having a maximum VOC level of 55%. Moreover, they are easy to remove on washing and produce, at the outlet of the sprayer, a spray, a lacquer or a foam with an appearance which is satisfactory for cosmetic purposes.

The compositions in accordance with the invention comprise, in a cosmetically acceptable aqueous medium, at least one film-forming acrylic oligomer, which is soluble or dispersible in the aqueous medium, having a molecular weight, measured by steric exclusion chromatography, of less than or equal to 50,000 and with a glass transition temperature Tg ranging from 0 to 45° C. and which is capable of being obtained by polymerization of a mixture of monomers comprising:

a) preferably from 20 to 45 by weight % of at least one monomer (A) selected from tert-butyl methacrylate, tert-butylacrylate, and isobutyl methacrylate, relative to the total weight of the oligomer;

b) preferably from 5 to 25 by weight % of at least one monomer (B) with ethylenic unsaturation comprising at least one carboxylic acid functional group, relative to the total weight of the oligomer;

c) at least one monomer (C) of the ($C_1$–$C_4$)alkyl acrylate type, other than tert-butyl acrylate, in an amount which is sufficient to produce an oligomer having a Tg temperature ranging from 0 to 45° C.

After polymerization, of course, the oligomer comprises a mixture of residues of the monomers defined in a), b), and c). Further, when monomers (A) and (B) are utilized in amounts outside the preferred ranges defined above, the amount of monomers (A), (B), and (C) is sufficient to produce an oligomer having a Tg temperature ranging from 0 to 45° C.

The at least one monomer (B) is selected from, for example:

monocarboxylic acids with ethylenic unsaturation, such as acrylic acid, methacrylic acid and crotonic acid;

dicarboxylic acids with ethylenic unsaturation, such as maleic acid, fumaric acid, itaconic acid and their monoester or monoamide derivatives with a $C_1$–$C_4$ alkyl group; and allyloxyacetic acid.

Use is more preferably made of acrylic acid, alone or as a mixture with methacrylic acid. The at least one monomer (B) is very preferably present in a concentration ranging from 8 to 15% by weight with respect to the total weight of the oligomer.

The at least one monomer (C) is preferably isobutyl acrylate.

According to a specific form of the invention, use is made, for the preparation of the oligomer, of at least one complementary monomer (D) with ethylenic unsaturation which is copolymerizable with the monomers (A), (B) and (C) and which is chosen so that the Tg temperature of the final oligomer ranges from 0 to 45° C. The concentration of at least one monomer (D) preferably varies from 0 to 10% by weight with respect to the total weight of the oligomer.

The at least one monomer (D) can be selected from, for example:
vinyl acetate;
vinyl propionate;
N-vinylpyrrolidone;
hydroxyethyl (meth)acrylate;
2-hydroxypropyl (meth)acrylate;
methoxyethyl (meth)acrylate;
ethoxyethyl (meth)acrylate; and
N,N-dimethylacrylamide.

The oligomers which are soluble or dispersible in the aqueous medium of the compositions of the invention preferably have a molecular weight, measured by steric exclusion chromatography, ranging from 500 to 45,000.

The oligomers which are soluble or dispersible in the aqueous medium of the compositions of the invention preferably have a glass transition temperature Tg ranging from 0 to +45° C., more preferably from +10 to +35° C.

The film-forming acrylic oligomers according to the invention can be prepared conventionally by solution, suspension or emulsion radical polymerization or copolymerization.

The film-forming acrylic oligomers according to the invention are preferably prepared in solution in an organic solvent from the appropriate monomers in the presence of a free-radical initiator. They can then be purified by precipitation from a solvent, such as petroleum ether.

The preparation can also be carried out semi-continuously, use being made of a vessel heel containing only the solvent part, a small part of the mixture of monomers and a part of the initiator. Heating is then carried out to the reaction temperature and a double addition is carried out simultaneously of the remainder of the mixture of the monomers and of the remainder of the initiator, dissolved in an amount of solvent.

The film-forming acrylic oligomers of the invention can then be partially or completely neutralized by a non-volatile monobasic compound, such as an inorganic base, for example sodium hydroxide or potassium hydroxide, or an aminoalcohol, for example taken from the group selected from 2-amino-2-methyl-1-propanol (AMP), triethanolamine, triisopropanolamine (TIPA), monoethanolamine, tri[(2-hydroxy)-1-propyl]amine, 2-amino-2-methyl-1,3-propanediol (AMPD) or 2-amino-2-hydroxymethyl-1,3-propanediol.

The cosmetically acceptable aqueous medium of the invention is preferably composed of water or a mixture of water and at least one cosmetically acceptable solvent which is compatible with the film-forming acrylic oligomer of the invention, such as a monoalcohol, a polyalcohol, a glycol ether, acetone or an ester, alone or in the form of a mixture.

The cosmetically acceptable aqueous medium of the invention is more preferably composed of water or of water and a lower $C_1$–$C_4$ alcohol, such as ethanol or isopropanol.

The concentration of organic solvent in the composition of the invention preferably ranges from 15 to 35 weight %, and more preferably from 20 to 30 weight%, with respect to the total weight of the composition.

When the composition according to the invention is packaged under pressure in an aerosol device for the purposes of obtaining a lacquer, it comprises at least one propellant agent which can be selected from volatile hydrocarbons, such as n-butane, propane, isobutane or pentane, or chlorinated and/or fluorinated hydrocarbons and their mixtures, carbon dioxide gas, nitrous oxide, dimethyl ether, nitrogen and compressed air.

The concentration of the propellant gas in the aerosol device depends on the nature of the propellant selected.

Dimethyl ether is particularly preferred. It is used in the aerosol lacquers of the invention as a propellant gas in concentrations preferably ranging from 30 to 45 weight % with respect to the total weight of the composition.

The concentration of volatile organic compound (VOC) in a composition according to the invention packaged in the form of an aerosol or of a pump-action spray is preferably less than or equal to 55 weight %, and more preferably ranges from 30 to 55 weight % with respect to the total weight of the formulation packaged as an aerosol or as a pump-action spray.

The pH of the compositions according to the invention generally ranges from 2 to 9, and more preferably from 3 to 8. The compositions according to the invention can be adjusted to the chosen value by means of basifying or acidifying agents commonly used in cosmetics.

The compositions according to the invention can, in addition, optionally include at least one plasticizing agent in order to improve the mechanical properties, the cosmetic properties and the adhesion to hair of the deposited film-forming acrylic oligomer after application and drying. The presence of a plasticizing agent for adjusting the lacquering power in the lacquer formulations of the invention, is optional, in contrast to conventional lacquer formulations.

Mention may be made, among plasticizing agents which may be used according to the invention, of:
Carbitols from the Company Union Carbide, namely Carbitol or diethylene glycol ethyl ether, methyl Carbitol or diethylene glycol methyl ether, butyl Carbitol or diethylene glycol butyl ether or alternatively hexyl Carbitol or diethylene glycol hexyl ether,
Cellosolves from the Company Union Carbide, namely Cellosolve or ethylene glycol ethyl ether, butyl Cellosolve or ethylene glycol butyl ether or hexyl Cellosolve or ethylene glycol hexyl ether, propylene glycol derivatives and in particular propylene glycol phenyl ether, propylene glycol diacetate, dipropylene glycol butyl ether or tripropylene glycol butyl ether, as well as Dowanols from the Company Dow Chemical, namely Dowanol PM or propylene glycol methyl ether, Dowanol DPM or dipropylene glycol methyl ether and Dowanol TPM or tripropylene glycol methyl ether.

Mention may also be made of:
diethylene glycol methyl ether or Dowanol DM from the Company Dow Chemical,
castor oil oxyethylenated with 40 mol of ethylene oxide, such as that sold by the Company Rhône-Poulenc under the name of "Mulgofen LE-719",
benzyl alcohol,
triethyl citrate sold by the Company Pfizer under the name of "Citroflex-2", 1,3-butylene glycol, diethyl, dibutyl and diisopropyl phthalates and adipates, diethyl and dibutyl tartrates, diethyl, dibutyl and di(2-ethylhexyl) phosphates, and glycerol esters, such as glyceryl diacetate (diacetin) and glyceryl triacetate (triacetin).

The at least one plasticizing agent is more preferably selected from those which are hydrophilic or water-soluble.

The at least one plasticizing agent is present in a proportion preferentially ranging from 0 to 20% by weight, relative to the weight of the film-forming oligomer. This proportion varies according to the application envisaged.

The compositions according to the invention as defined above can be used as styling products for hair shaping and/or form retention of the hairstyle packaged as aerosol lacquers, pump-action sprays for fixing the hair or styling aerosol foams.

The hair compositions for form retention of the hairstyle in accordance with the present invention preferably include the film-forming acrylic oligomer in a concentration ranging from 3 to 20% by weight, on a dry basis, with respect to the total weight of the composition.

The hair compositions in accordance with the invention may additionally include conventional cosmetic additives, such as preservatives, softeners, sequestering agents, fragrances, dyes, viscosity modifiers, pearlescence agents, moisturizing agents, antidandruff agents, antiseborrhoeic agents, sunscreening agents, hair-conditioning agents, antioxidants, proteins or vitamins.

Another subject of the invention comprises a non-therapeutic process for hair shaping and/or form retention of hair, comprising the step of directly applying a composition as defined above to the hair.

The following examples serve to illustrate the invention without, however, limiting it.

EXAMPLES

Example 1: Preparation of a compatible film-forming acrylic oligomer in a water/ethanol/DME aerosol lacquer medium with a maximum VOC level of 55%

| Composition of the oligomer: | | |
|---|---|---|
| tert-butyl acrylate | (A) | 40 weight % |
| acrylic acid | (B) | 10 weight % |
| isobutyl acrylate | (C) | 50 weight % |

Procedure:

The following mixture was introduced into a cylindrical reactor with central mechanical stirring, a thermometer and a reflux condenser under a stream of nitrogen:

| | |
|---|---|
| isobutyl acrylate | 50 g |
| tert-butyl acrylate | 40 g |
| methacrylic acid | 10 g |
| azobisisobutylacrylonitrile (initiator) | 2 g |
| ethanol | 200 g |

The mixture was brought, with stirring and under a stream of nitrogen, to reflux of the ethanol (78° C.). The mixture was allowed to react for 12 hours under these conditions. The mixture was brought back to room temperature. The polymer was then purified by precipitation of the alcoholic solution from 5 l of petroleum ether. The precipitate was then dried until a constant weight was obtained.

The yield obtained after drying was 90%. The acid number obtained was 81.5. The molecular weight at the tip of the peak measured by steric exclusion chromatography was 36,800 (elution in tetrahydrofuran with respect to polystyrene standards). The Tg temperature, measured by DSC (Differential Scanning Calorimetry), is 27° C.

A concentrated alcoholic oligomer solution, 100% neutralized by 2-amino-2-methyl-1-propanol (AMP), was prepared from the following mixture:

| | |
|---|---|
| Oligomer | 100 g |
| AMP | 12.44 g |
| Ethanol | 112.44 g |

Stirring was carried out for 24 hours at room temperature. A solution containing 50% weight, on a dry basis, of oligomer was thus obtained.

Example 2: Water/ethanol/DME aerosol lacquer containing 45% of VOC for fixing hair containing the acrylic oligomer of Example 1

| COMPOSITION BEFORE PACKAGING: | |
|---|---|
| Alcoholic solution containing 50% weight of oligomer of Example 2 | 14 g |
| Deionized water | 48 g |
| Ethanol | 8 g |
| AEROSOL LACQUER CONTAINING 45% OF VOC: | |
| Above composition | 70 g |
| Dimethyl ether | 30 g |

This lacquer contained 7% weight of solids.

After application to hair, an excellent lacquering power, a rapid drying time, good cosmetic properties, in particular with respect to feel and disentangling, and good removal of the deposit on shampooing were obtained.

Example 3: Water/ethanol/DME aerosol lacquer containing 45% of VOC for hair fixing containing the acrylic oligomer of Example 1

| COMPOSITION BEFORE PACKAGING: | |
|---|---|
| Alcoholic solution containing 50% weight of oligomer of Example 1 | 21.0 g |
| Deionized water | 44.5 g |
| Ethanol | 4.5 g |
| AEROSOL LACQUER CONTAINING 45% OF VOC: | |
| Above composition | 70 g |
| Dimethyl ether | 30 g |

This lacquer contained 7% weight of solids.

After application to hair, an excellent lacquering power, a rapid drying time, good cosmetic properties, in particular with respect to feel and disentangling, and good removal of the deposit on shampooing were obtained.

We claim:

1. A composition for hair shaping and/or form retention of hair, comprising, in a cosmetically acceptable aqueous medium, at least one film-forming acrylic oligomer, which is soluble or dispersible in said aqueous medium, having a molecular weight of less than or equal to 50,000 and with a glass transition temperature Tg ranging from 0° C. to 45° C., wherein said at least one film-forming acrylic oligomer comprises:
a) at least one residue of monomer (A) selected from tert-butyl methacrylate, tert-butyl acrylate, and isobutyl methacrylate;
b) at least one residue of monomer (B) with ethylenic unsaturation comprising at least one carboxylic acid functional group; and
c) at least one residue of monomer (C) comprising a ($C_1$–$C_4$)alkyl acrylate, said residues of monomers (A), (B) and (C) being present in an amount sufficient to produce an oligomer having a Tg temperature ranging from 0 to 45° C.,
wherein monomer (C) is not tert-butyl acrylate.

2. A composition according to claim 1, wherein said at least one film-forming acrylic oligomer has a molecular weight measured by steric exclusion chromatography of less than or equal to 50,000, and comprises:
a) from 20 to 45% by weight, relative to the total weight of said at least one film-forming acrylic oligomer, of at least one residue of monomer (A) selected from tert-butyl methacrylate, tert-butyl acrylate, and isobutyl methacrylate;
b) from 5 to 25% by weight, relative to the total weight of said at least one film-forming acrylic oligomer, of at least one residue of monomer (B) with ethylenic unsaturation comprising at least one carboxylic acid functional group; and
c) at least one residue of monomer (C) comprising a ($C_1$–$C_4$)alkyl acrylate, said residue of monomer (C) being present in an amount sufficient to produce an oligomer having a Tg temperature ranging from 0 to 45° C.

3. A composition according to claim 2, wherein said at least one residue of monomer (B) is present in a concentration, ranging from 8 to 15% by weight, relative to the total weight of at least one film-forming acrylic oligomer.

4. A composition according to claim 1, wherein said monomer (B) is selected from:
monocarboxylic acids with ethylenic unsaturation;
dicarboxylic acids with ethylenic unsaturation; and
allyloxyacetic acid.

5. A composition according to claim 1, wherein said monomer (B) is selected from acrylic acid and methacrylic acid.

6. A composition according to claim 1, wherein said monomer (C) is isobutyl acrylate.

7. A composition according to claim 1, wherein said at least one film-forming acrylic oligomer additionally comprises at least one residue of a complementary monomer (D) with ethylenic unsaturation, and wherein said at least one film-forming acrylic oligomer comprising said at least one residue of monomer (A), said at least one residue of monomer (B), said at least one residue of monomer (C), and said at least one residue of complementary monomer (D) has a Tg temperature ranging from 0 to 45° C., and further wherein said complementary monomer (D) is different from said monomer (B).

8. A composition according to claim 7, wherein said at least one residue of complementary monomer (D) is present in a concentration ranging up to 10% by weight, relative to the total weight of said at least one film-forming acrylic oligomer.

9. A composition according to claim 7, wherein said monomer (D) is selected from:

vinyl acetate;
vinyl propionate;
N-vinylpyrrolidone;
hydroxyethyl (meth)acrylate;
2-hydroxypropyl (meth)acrylate;
methoxyethyl (meth)acrylate;
ethoxyethyl (meth)acrylate; and
N,N-dimethylacrylamide.

10. A composition according to claim 1, wherein said at least one film-forming acrylic oligomer has a molecular weight, measured by steric exclusion chromatography, ranging from 500 to 45,000.

11. A composition according to claim 10, wherein said at least one film-forming acrylic oligomer has a glass transition temperature Tg ranging from 10° C. to 35° C.

12. A composition according to claim 1, wherein said cosmetically acceptable aqueous medium is selected from water and a mixture of water and at least one cosmetically acceptable solvent compatible with said at least one film-forming acrylic oligomer.

13. A composition according to claim 12, wherein said at least one cosmetically acceptable solvent is selected from monoalcohols, polyalcohols, glycol ethers, acetone, and fatty acid esters.

14. A composition according to claim 12, wherein said cosmetically acceptable aqueous medium is selected from water and a mixture of water and a $C_1$–$C_4$ alcohol.

15. A composition according to claim 14, wherein said $C_1$–$C_4$ alcohol is selected from ethanol and isopropanol.

16. A composition according to claim 12, wherein said at least one cosmetically acceptable solvent compatible with said at least one film-forming acrylic oligomer is present in a concentration ranging from 15 to 35% by weight, relative to the total weight of said composition.

17. A composition according to claim 16, wherein said at least one cosmetically acceptable solvent compatible with said at least one film-forming acrylic oligomer is present in a concentration ranging from 20 to 30% by weight, relative to the total weight of said composition.

18. A composition according to claim 1, wherein said composition is packaged in a form selected from an aerosol device under pressure and a pump-action spray.

19. A composition according to claim 18, wherein said composition is packaged in an aerosol device under pressure in the presence of at least one propellant agent.

20. A composition according to claim 19, wherein said at least one propellant agent is selected from volatile hydrocarbons, chlorinated hydrocarbons, fluorinated hydrocarbons, carbon dioxide gas, nitrous oxide, dimethyl ether, nitrogen and compressed air.

21. A composition according to claim 20, wherein said at least one propellant agent is dimethyl ether.

22. A composition according to claim 21, wherein said dimethyl ether is present in a concentration ranging from 30 to 45% by weight, relative to the total weight of said composition.

23. A composition according to claim 18, wherein said composition further comprises at least one volatile organic compound, and wherein the concentration of said at least one volatile organic compound is less than or equal to 55% by weight, relative to the total weight of said composition.

24. A composition according to claim 23, wherein said concentration of said at least one volatile organic compound ranges from 30 to 55% by weight, relative to the total weight of said composition.

25. A composition according to claim 1, wherein said composition has a pH ranging from 2 to 9.

26. A composition according to claim 25, wherein said composition has a pH ranging from 3 to 8.

27. A composition according to claim 1, wherein said composition further comprises at least one plasticizing agent.

28. A composition according to claim 27, wherein said at least one plasiticizing agent is selected from hydrophilic plasticizing agents and water-soluble plasticizing agents.

29. A composition according to claim 27, wherein said at least one plasticizing agent is present in a concentration ranging up to 20% by weight, relative to the weight of said at least one film-forming acrylic oligomer.

30. A composition according to claim 1, wherein said composition is in the form selected from aerosol lacquers, pump-action sprays, and styling aerosol foams.

31. A composition according to claim 1, wherein said at least one film-forming acrylic film-forming oligomer is present in a concentration ranging from 3 to 20%, by weight, on a dry basis, relative to the total weight of the composition.

32. A composition according to claim 1, wherein said composition further comprises at least one adjuvant.

33. A non-therapeutic process for hair shaping and/or for fixing hair, comprising the step of:

applying a composition according to claim 1 to said hair.

34. A composition for hair shaping and/or form retention of hair, comprising, in a cosmetically acceptable aqueous medium, at least one film-forming acrylic oligomer, which is soluble or dispersible in said aqueous medium, having a molecular weight, measured by steric exclusion chromatography, of less than or equal to 50,000 and with a glass transition temperature Tg ranging from 0° C. to 45° C., wherein said at least one film-forming acrylic oligomer is obtained from the polymerization of:

a) at least one monomer (A) selected from tert-butyl methacrylate, tert-butyl acrylate, and isobutyl methacrylate;

b) at least one monomer (B) with ethylenic unsaturation comprising at least one carboxylic acid functional group; and c) at least one monomer (C) comprising a $(C_1-C_4)$alkyl acrylate, said monomers (A), (B) and (C) being present in an amount sufficient to produce an oligomer having a Tg temperature ranging from 0 to 45° C., wherein monomer (C) is not tert-butyl acrylate.

35. A composition for hair shaping and/or form retention of hair, comprising, in a cosmetically acceptable aqueous medium, at least one film-forming acrylic oligomer, which is soluble or dispersible in said aqueous medium, having a molecular weight, measured by steric exclusion chromatography, of less than or equal to 50,000 and with a glass transition temperature Tg ranging from 0° C. to 45° C., wherein said at least one film-forming acrylic oligomer is obtained from the polymerization of:

a) at least one monomer (A) selected from tert-butyl methacrylate, tert-butyl acrylate, and isobutyl methacrylate;

b) at least one monomer (B) with ethylenic unsaturation comprising at least one carboxylic acid functional group;

c) at least one monomer (C) comprising a $(C_1-C_4)$alkyl acrylate, said monomers (A), (B) and (C) being present in an amount sufficient to produce an oligomer having a Tg temperature ranging from 0 to 45° C., wherein monomer (C) is not tert-butyl acrylate; and d) at least one complementary monomer (D) with ethylenic unsaturation, wherein said at least one complementary monomer (D) is different from said at least one monomer (B).

* * * * *